United States Patent [19]

Muldrow, Jr.

[11] 4,249,534
[45] Feb. 10, 1981

[54] APPARATUS FOR BREAKING SCAR TISSUE WITHIN A HUMAN BODY

[76] Inventor: Louis M. Muldrow, Jr., 750 Shaker Dr., Lexington, Ky. 40504

[21] Appl. No.: 30,104

[22] Filed: Apr. 16, 1979

[51] Int. Cl.³ ............................................. A61B 17/00
[52] U.S. Cl. ...................................... 128/319; 128/59
[58] Field of Search ................................... 128/59–61, 128/320, 346, 355, 319

[56] References Cited

U.S. PATENT DOCUMENTS

| | | | |
|---|---|---|---|
| 718,766 | 1/1903 | Ingram | 128/61 |
| 1,795,073 | 3/1931 | Brown | 128/61 UX |
| 1,795,580 | 3/1931 | Trump | 128/319 |
| 2,232,493 | 2/1941 | Stuckey et al. | 128/61 |
| 2,714,381 | 8/1955 | Corley et al. | 128/61 |
| 3,503,388 | 3/1970 | Cook | 128/60 X |

Primary Examiner—John D. Yasko
Attorney, Agent, or Firm—Frank C. Leach, Jr.

[57] ABSTRACT

A plurality of arms is pivotally mounted on a support so that the arms may be moved simultaneously towards a central axis to produce a continuously increasing and radially symmetrical force of substantially the same magnitude at each of a plurality of points around an area of the human body having scar tissue so that precisely controlled opposed forces are produced. The arms can have their force exerting plane changed through their mounting arrangement on a carrier, which is mounted for horizontal sliding movement above the patient. The carrier is mounted on support means, which can be moved vertically to move the engaging arms into engagement with the area having the scar tissue.

35 Claims, 8 Drawing Figures

APPARATUS FOR BREAKING SCAR TISSUE WITHIN A HUMAN BODY

In plastic surgery, a silicone bag is implanted within the human body beneath a human breast for aesthetic purposes. As with any foreign matter within the human body, scar tissue is produced around the silicone bag implant by the human body. In some patients, scar capsules, which surround the silicone bag implant, result in tight, deforming, painful, and firm qualities in the area of the human breast. Since the patient seeks a human breast having a soft and natural feel to the touch so that the presence of the silicone bag implant cannot be felt, it is necessary to be able to break this scar tissue by rupturing or opening the scar capsules surrounding the silicone bag implant.

Furthermore, these qualities in the area of the human breast can cause pain because of the tightness of the scar capsules, social embarrassment because of the hardness, and inability to assume or great discomfort in the prone position (i.e., sleeping). These are additional reasons why it is necessary to rupture the scar capsules.

Plastic surgeons have previously broken the scar tissue through usually applying forces by their hands to the area having the scar tissue. This has had the disadvantage of the surgeon being unable to stop the application of the forces as soon as the scar tissue breaks as is evidenced by a popping sound and/or a reduction in firmness. As a result, the high forces being applied through the hands of the surgeon or with some mechanical device has occasionally resulted in the surgeon having a finger or thumb broken or dislocated when attempting rupture of the scar capsules by the application of such high forces. Even if a finger or thumb is not broken, it may be bruised or sprained in many instances.

Furthermore, continued application of the force beyond the time of rupture of the scar capsules may result in rupture of the silicone bag. This causes deflation of the bag implant. As a result of the deflation by rupture of the bag, the material within the bag may extrude therefrom into the surrounding body area.

The apparatus of the present invention overcomes the foregoing problems through applying radially symmetrical forces, which are preferably opposed, controlled by the surgeon without harm to the surgeon or rupture of the silicone bag by allowing the surgeon to stop the application of the forces as soon as the scar capsules break. The breaking of the scar capsules is readily recognized by the surgeon since it produces a reduction of resistance to the application of the forces, and this is felt by the surgeon. There also is usually a popping sound at this time.

The apparatus of the present invention accomplishes this through providing a plurality of arms for engaging a plurality of portions or positions around the area having the scar tissue. The arms are moved towards a central axis to produce continuously increasing and radially symmetrical forces, which are preferably opposed, on the scar tissue.

An object of this invention is to provide an apparatus for breaking scar tissue within a human body.

Another object of this invention is to apply a continuously increasing and radially symmetrical force of substantially the same magnitude to various portions around an area of scar tissue within a human body.

A further object of this invention is to apply continuously increasing opposed forces to various portions around an area of scar tissue within a human body.

Other objects of this invention will be readily perceived from the following description, claims, and drawings.

This invention relates to an apparatus for breaking scar tissue within a human body. The apparatus includes force applying means to apply a continuous and increasing radially symmetrical force of substantially the same magnitude at each of a plurality of portions around an area having the scar tissue until the scar tissue breaks.

The attached drawings illustrate a preferred embodiment of the invention, in which.

Figures 1, 4, 5, 7:
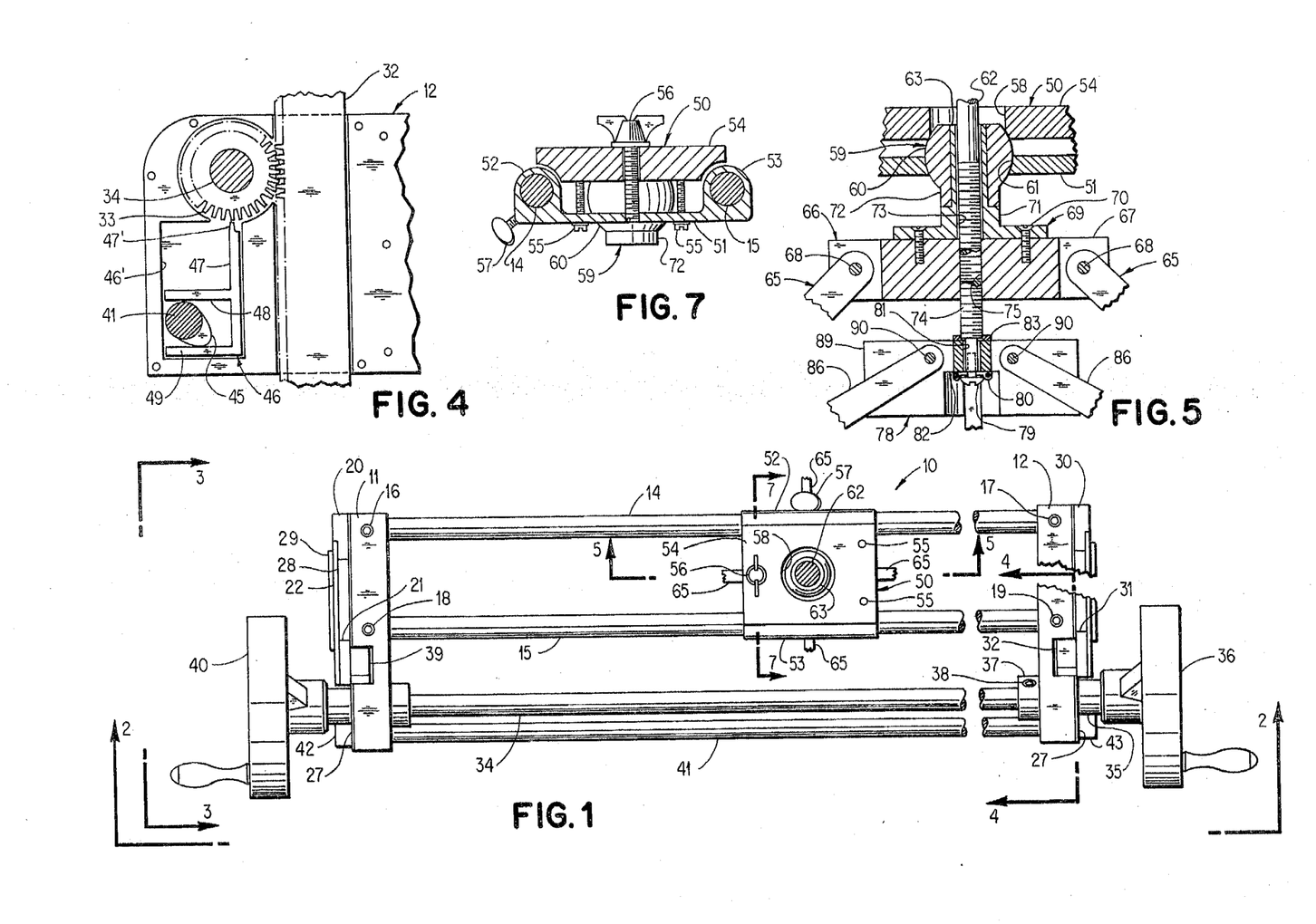
FIG. 1 is a top plan view of the apparatus of the present invention for breaking scar tissue.
FIG. 4 is a fragmentary elevational view, partly in section, of one of the housings of the apparatus of the present invention and taken along line 4—4 of FIG. 1.
FIG. 5 is a fragmentary sectional view, partly in elevation, of a portion of the apparatus of FIG. 1 showing a portion of an actuation mechanism for applying forces to break the scar tissue and taken along line 5—5 of FIG. 1.
FIG. 7 is a sectional view, partly in elevation, of the carrier of the apparatus of FIG. 1 and taken along line 7—7 of FIG. 1.

Referring to the drawings and particularly FIG. 1, there is shown an apparatus 10 for breaking scar tissue within a human body, particularly for breaking scar tissue produced around an implanted silicone bag within a human breast. The apparatus 10 includes a pair of housings 11 and 12, which are connected to each other by a pair of substantially parallel rods 14 and 15.

The rod 14 has one end secured to the housing 11 by a screw 16 and its other end secured to the housing 12 by a screw 17. Similarly, the rod 15 is secured to the housing 11 by a screw 18 and to the housing 12 by a screw 19.

The housing 11 is slidably mounted on a pair of vertically disposed legs 20 and 21. The upper ends of the legs 20 and 21 are connected to each other by a plate 22 (see FIG. 3). The legs 20 and 21 also are connected to each other by a bar 23 attached to their inner surfaces and a plate 24 connected to their outer surfaces.

Figure 3:
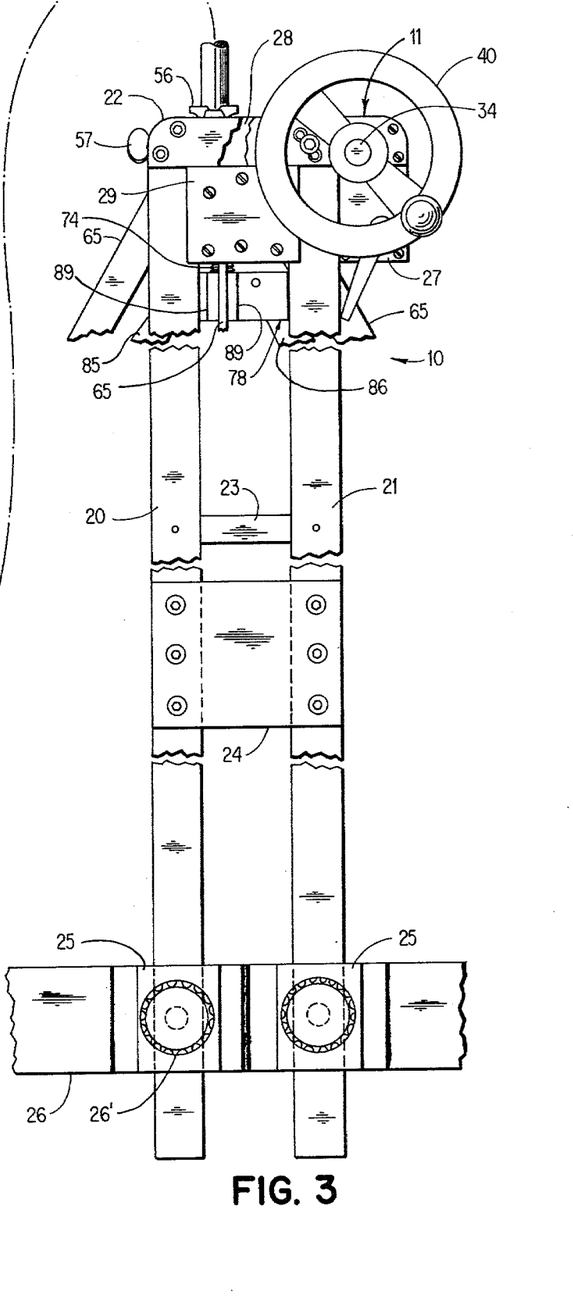
FIG. 3 is an end elevational view of the apparatus of FIG. 1 and taken along line 3—3 of FIG. 1 and showing the arrangement for mounting the apparatus on an operating table.

Each of the legs 20 and 21 has its lower portion extending through a U-shaped support bracket 25 on a side of an operating table 26. Each of the brackets 25 has a clamping screw 26' supported thereby to engage each of the legs 20 and 21 to position the apparatus 10 in the desired vertical position above the operating table 26 by locking the legs 20 and 21 to the sides of the operating table 26.

The housing 11 has a bearing structure mounted thereon to enable sliding of the housing 11 along the legs 20 and 21. The bearing structure, which is formed of a suitable plastic such as nylon, for example, includes a relatively thin plate 27 (see FIGS. 1 and 2) secured to the outer surface of the housing 11. The plate 27 slides along the inner surface of each of the legs 20 and 21.

A bearing block 28 (see FIG. 1) is secured to the plate 27 and is disposed between inner side surfaces of the legs 20 and 21. A bearing plate 29 (see FIGS. 1 and 3) is mounted on the outer surface of the lower portion of the bearing block 28 and slides along a portion of the outer surface of each of the legs 20 and 21 as shown in FIG. 3.

The uppermost movement of the housing 11 is stopped by engagement of the upper surface of the bearing plate 29 with the lower surface of the leg connector plate 22 as shown in FIG. 3. Downward movement of the housing 11 is stopped by engagement of the bottom surface of the bearing plate 27 and the bottom surface of the housing 11 with the upper surface of the leg connector bar 23.

The housing 12 (see FIG. 1) is slidably supported on a pair of vertically disposed legs 30 and 31 in the same manner as the housing 11. The legs 30 and 31 are supported on the opposite side of the operating table 26 (see FIG. 3) to the legs 20 And 21 in the same manner as the legs 20 and 21.

The leg 31 (see FIG. 2) has a rack 32 secured to its inner surface by screws at its upper and lower ends. As shown in FIG. 4, the teeth of the rack 32 mesh with the teeth of a gear 33, which is fixedly mounted on a horizontally disposed shaft 34 for rotation therewith. The gear 33 is disposed within the housing 12.

The shaft 34 is rotatably supported in the end walls of each of the housings 11 (see FIG. 1) and 12 and extends therebetween. The shaft 34 is substantially parallel to each of the rods 14 and 15 as shown in FIG. 1 and is in substantially the same horizontal plane.

The shaft 34 extends beyond the outer end wall of the housing 12 and has a spacer sleeve 35 mounted thereon. The sleeve 35 spaces a handle wheel 36, which is secured to the shaft 34 by a set screw (not shown), from the remainder of the structure as shown in FIG. 1.

A bearing collar 37 is fixed to the shaft 34 by a set screw 38. The bearing collar 37 bears against the inner end wall of the housing 12.

The housing 11 has a gear (not shown) therein mounted on the shaft 34 for rotation therewith. The gear meshes with a rack 39 mounted on the leg 21. A handle wheel 40 is secured to the shaft 34 in the same manner as the handle wheel 36. Accordingly, when the handle wheels 36 and 40 are rotated, the housing 11 is moved up or down along the legs 20 and 21 through the gear within the housing 11 cooperating with the rack 39 and the housing 12 is similarly moved along the legs 30 and 31 through cooperation of the gear 33 (see FIG. 4) within the housing 12 with the rack 32.

Figure 2:
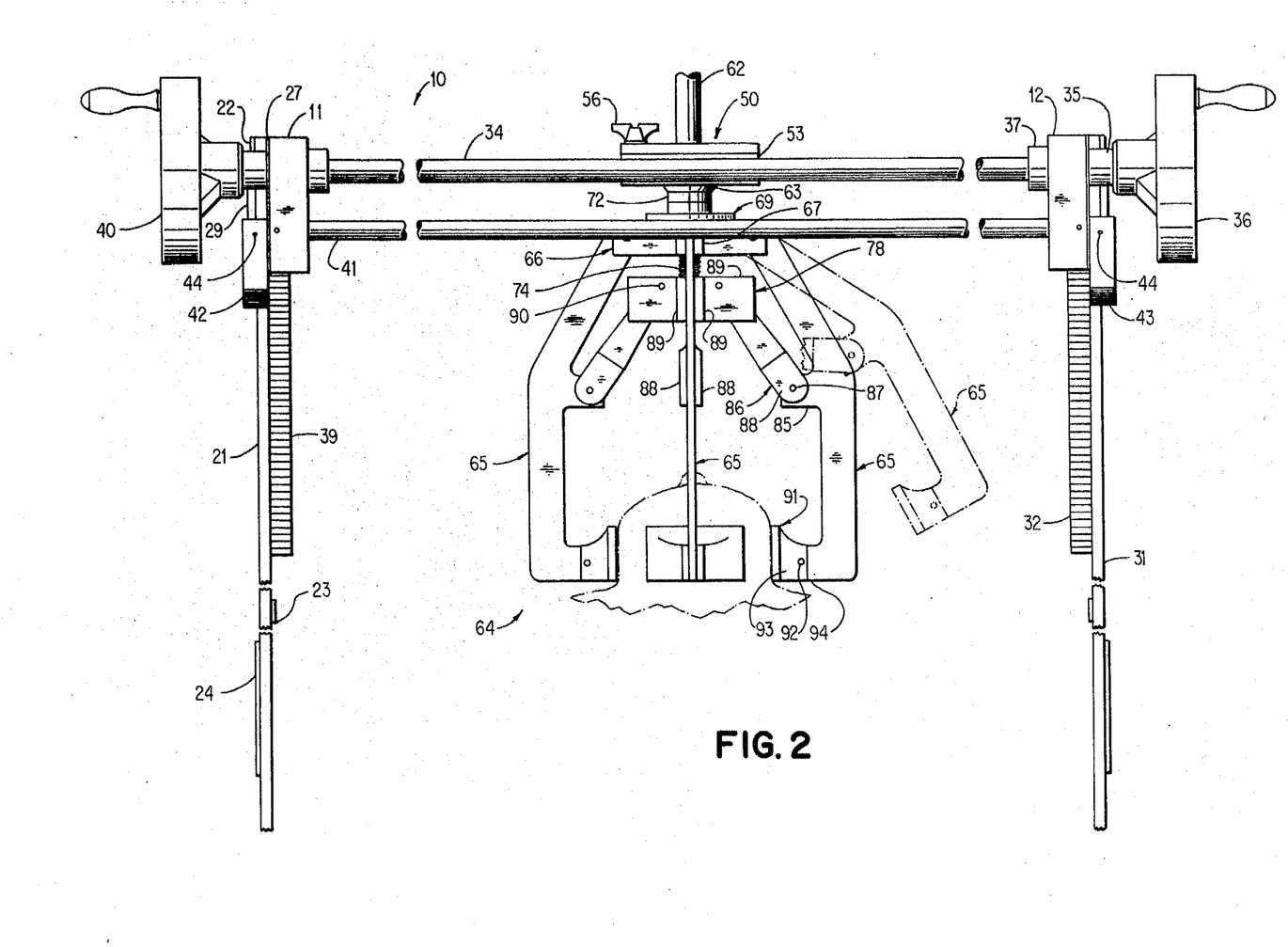
FIG. 2 is a side elevational view of the apparatus of FIG. 1 and taken along line 2—2 of FIG. 1.

A rod 41 (see FIGS. 1 and 2), which is disposed beneath the horizontal plane containing the rods 14 and 15 and the shaft 34, extends through each of the housings 11 and 12. The rod 41 has actuating arms 42 and 43 at its ends adjacent the housings 11 and 12, respectively, as shown in FIG. 2. Each of the arms 42 and 43 is secured to the rod 41 by a set screw 44.

As shown in FIG. 4, the rod 41 has a cam 45 mounted thereon within the housing 12 for cooperation with a lock 46. The lock 46 is slidably disposed in a recess 46' in the housing 12.

When the rod 41 is rotated counterclockwise (as viewed in FIG. 4), the lock 46 moves vertically through having a finger 47 slide along a side wall of the recess 46' in the housing 12 so that a projection 47' on the end of the finger 47 is moved between two of the teeth on the gear 33 whereby the gear 33 is locked to hold the housing 12 in the desired position on the rack 32. The cam 45 engages the bottom surface of a finger 48, which has its end slide along a side wall of the recess 46' to aid in guiding the lock 46 vertically, to lift the lock 46 vertically.

When the housing 12 is to be released from its locking relation with the rack 32, the rod 41 is rotated clockwise (as viewed in FIG. 4) to the position of FIG. 4 during which the cam 45 engages the upper surface of a finger 49, which is parallel to the finger 48 and has its end engaging the same side wall of the recess 46' as the end of the finger 48 to aid in guiding the lock 46 vertically, of the lock 46. This withdraws the projection 47' on the end of the finger 47 from disposition between two of the teeth on the gear 33.

A similar construction exists within the housing 11 (see FIG. 2) to enable the housing 11 to be locked to the rack 39. Thus, the housings 11 and 12 are held at any desired vertical position along the racks 39 and 32, respectively.

The horizontally disposed rods 14 (see FIG. 1) and 15 have a carrier 50 slidably mounted thereon. The carrier 50 includes a base plate 51 (see FIG. 7) having cylindrical bearing positions 52 and 53 sliding on the rods 14 and 15, respectively. The carrier 50 has an upper plate 54, which is secured at one side to the base plate 51 by a pair of screws 55 and at its other end by a locking screw 56.

Thus, the carrier 50 is slidably movable along the parallel rods 14 and 15 between the housings 11 (see FIG. 1) and 12. The carrier 50 is locked in any position to which it is moved by a locking screw 57 extending through the cylindrical bearing portion 52 to engage the rod 14. Release of the locking screw 57 enables movement of the carrier 50 along the horizontally disposed rods 14 and 15.

The upper plate 54 of the carrier 50 has an opening or passage 58 (see FIGS. 1 and 5) within which is disposed a portion of an element 59 having a spherical bearing portion 60 as shown in FIG. 5. The spherical bearing portion 60 also is disposed within an opening 61 in the base plate 51 of the carrier 50. The opening 61 has an arcuate or curved wall to conform to the spherical bearing portion 60.

The element 59 has a shaft 62 extending through a sleeve 63 within the element 59. The shaft 62 has a gripping mechanism 64 (see FIG. 2) supported on its lower end for engaging the area having the scar tissue to cause breaking thereof by applying radially symmetrical forces of substantially the same magnitude.

Accordingly, the gripping mechanism 64 is supported by the carrier 50 for tilting to various positions because of the spherical portion 60 (see FIG. 5) of the element 59 functioning as a ball and socket arrangement with the opening 61 and the lower portion of the opening 58 in the carrier 50. The tilting movement of the gripping mechanism 64 is limited by engagement of the shaft 62 with the upper edge of the circular shaped opening 58 in the upper plate 54 of the carrier 50.

Since the carrier 50 is mounted for sliding movement along the horizontally disposed rods 14 (see FIG. 1) and 15, the gripping mechanism 64 (see FIG. 2) can be moved to any horizontal position between the housings 11 and 12. Likewise, the vertical movement of the housings 11 and 12 through simultaneous rotation of the handle wheels 36 and 40 vertically moves the gripping mechanism 64.

The gripping mechanism 64 includes four arms 65 equally angularly spaced from each other. Thus, each of the arms 65 is 90° from each of the two adjacent arms 65.

The upper end of each of the arms 65 is pivotally connected to a block 66. Each of the arms 65 has its upper end disposed between bifurcated portions 67 of the block 66 and pivotally connected thereto by a pivot pin 68 (see FIG. 5).

The block 66 has its upper surface resting against the bottom surface of an annular plate 69 and secured to the annular plate 69 by four equally angularly spaced screws 70 (two shown). The annular plate 69 has a cylindrical hub 71 with its outer surface being a continuation of the outer surface of a lower cylindrical portion 72 of the element 59.

The hub 71 has the sleeve 63 integral therewith with the sleeve 63 being secured to the lower portion 72 of the element 59 by screws (not shown). Thus, the annular plate 69 and the element 59 are secured to each other.

The annular plate 69 has a central passage or opening 73 extending therethrough to enable the shaft 62 to extend therethrough. The shaft 62 has a lower threaded portion 74, which engages a threaded hole 75 extending through the block 66. Thus, the shaft 62 can be advanced or retracted through the block 66 by turning a handle 76 (see FIG. 3), which is secured to the upper end of the shaft 62 by a locking screw 77.

The lower end of the shaft 62 is secured to a block 78 (see FIG. 5) by having its lower end reduced and formed with a threaded hole to receive a screw 79, which passes through a bearing ring 80 into the threaded hole in the reduced end of the shaft 62. The reduced lower end of the shaft 62 is disposed within an axial passage 81 in the block 78, which has a surface 82 against which the ring 80 bears. The block 78 has a washer 83 mounted on its upper end. Therefore, when the shaft 62 is rotated, the block 78 is moved longitudinally towards or away from the block 66.

Each of the arms 65 has an inwardly projecting portion 85 (see FIG. 2) intermediate its ends and to which the bottom end of a connecting lever 86 is pivotally connected by a pivot pin 87. The lower end of each of the levers 86 has a pair of bifurcated portions 88 disposed on opposite sides of the projecting portion 85 on the arm 65 to which the lever 86 is pivotally connected.

The upper end of each of the levers 86 extends between a pair of bifurcated portions 89 of the block 78. A pivot pin 90 extends through the upper end of each of the connecting levers 86 and each pair of the bifurcated portions 89 of the block 78 between which the connecting lever 86 is disposed to pivotally connect the upper end of each of the levers 86 to the block 78.

Figure 6:
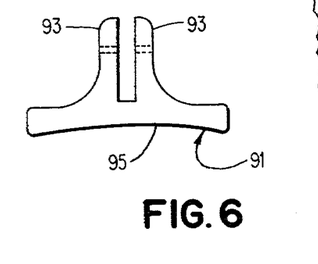
FIG. 6 is a top plan view of a body engaging gripper.
Figure 8:
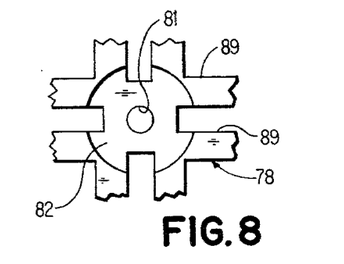
FIG. 8 is a fragmentary bottom plan view of a portion of a block of the present invention with the shaft and the arm connectors removed.

Each of the arms 65 has a gripper 91 pivotally mounted on its lower end by a pivot pin 92. Each of the grippers 91, which is preferably formed of a suitable plastic such as nylon, for example, has a pair of bifurcated portions 93 (see FIG. 6) disposed on opposite sides of a projecting portion 94 (see FIG. 2) at the bottom of each of the arms 65.

Each of the grippers 91 has a slightly curved or arcuate surface 95 (see FIG. 6), which engages the body of the patient at the area having the scar tissue. The plastic material of each of the grippers 91 is such that it will not damage the skin when the force is applied.

The upward movement of the block 78 (see FIG. 2) by rotation of the shaft 62 causes the arms 65 to pivot about the pivot pins 68 (see FIG. 5) to move the grippers 91 (see FIG. 2) radially towards each other and towards a central axis, which is defined by the longitudinal axis of the shaft 62. Thus, this applies a continuously increasing and radially symmetrical force of substantially the same magnitude at four equally angularly spaced portions around the area having the scar tissue. Rotation of the shaft 62 in the opposite direction withdraws the grippers 91 through moving the block 78 downwardly.

Considering the operation of the present invention, the apparatus 10 would be mounted above the operating table 26 (see FIG. 3) after the patient is lying on the operating table 26. The legs 20 and 21 and the legs 30 (see FIG. 1) and 31 are disposed in the brackets 25 (see FIG. 3) on opposite sides of the operating table 26 and retained therein by the clamping screws 26' with the apparatus 10 being at the desired vertical location relative to the patient. This is located so that the grippers 91 (see FIG. 2) are substantially close to the area having the scar tissue which is to be broken.

After the apparatus 10 has been supported on the operating table 26 (see FIG. 3), the locking screw 57 is released, and the carrier 50 (see FIG. 1) is moved horizontally along the rods 14 and 15 until the grippers 91 (see FIG. 2) are positioned substantially over the top of the area of the patient's body having the scar tissue. It should be understood that the arms 65 can be opened to a substantially larger degree (One of the arms 65 is shown at its maximum position in phantom in FIG. 2.). After the carrier 50 (see FIG. 1) has been moved along the rods 14 and 15 until the grippers 91 (see FIG. 2) are at the desired position, the carrier 50 is locked to the rod 14 (see FIG. 1) by the locking screw 57 to prevent horizontal movement thereof.

After the carrier 50 has been locked to the rod 14, the rod 41 is rotated to cause removal of the projection 47' (see FIG. 4) on the end of the finger 47 of the lock 46 from between two of the teeth of the gear 33 to unlock the housing 12 from the rack 32. The housing 11 (see FIG. 2) is unlocked from the rack 39 at the same time. This enables downward movement of the grippers 91 until they are adjacent the scar tissue area. This probably requires only a slight amount of vertical movement depending upon the position at which the apparatus 10 is supported on the operating table 26 (see FIG. 3).

As the grippers 91 (see FIG. 2) are positioned adjacent the area having the scar tissue, it may be necessary to dispose the grippers 91 in other than a substantially horizontal plane. It should be understood that the grippers 91 are moving radially in an arc so that they are only in a horizontal plane when all of the arms 65 are vertical. Accordingly, the locking screw 56 is released so that the element 59 is no longer clamped between the base plate 51 (see FIG. 7) and the upper plate 54 of the carrier 50. As a result, the shaft 62 may be tilted to tilt the engaging plane of the grippers 91 (see FIG. 2). This insures that the grippers 91 grip the scar tissue area at the desired portions of engagement. This is the area surrounding the silicone bag implant.

Then, the shaft 62 is rotated by the handle 76 (see FIG. 3) so that the block 78 (see FIG. 2) is moved upwardly towards the block 66. This moves the grippers 91 radially towards the central axis, which is defined by the longitudinal axis of the shaft 62. Thus, as the grippers 91 are moved towards each other by the upward movement of the block 78, an increasing radially symmetrical force of the same magnitude is applied by each of the grippers 91 to the area of the human body having the scar tissue.

When the scar tissue breaks, an immediate reduction in the opposed resistance to the application of the forces by the grippers 91 is perceived by the surgeon and a popping sound may be produced. As soon as this occurs, the surgeon ceases to turn the shaft 62 in a direction to advance the grippers 91 towards each other and rotates the shaft 62 in the opposite direction to release the forces applied by the grippers 91 on the scar tissue area.

The carrier 50 and the gripping mechanism 64 are then moved upwardly through rotating the handle wheels 36 and 40 simultaneously after the rod 41 has been rotated clockwise (as viewed in FIG. 4) to unlock the housing 12 from the rack 32 through releasing the projection 47' on the end of the finger 47 of the lock 46 from between two of the teeth of the gear 31. The housing 11 is similarly unlocked from the rack 32. The housings 11 and 12 would be normally returned to their uppermost positions before the rod 41 is rotated counterclockwise (as viewed in FIG. 4) to again lock the housing 12 to the rack 32 and the housing 11 to the rack 39.

Then, the apparatus 10 is removed from the operating table 26 (see FIG. 3) through releasing the screws 26'. Thus, this enables relatively quick removal of the apparatus 10 from the operating table 26.

An advantage of this invention is that scar tissue within a human body can be effectively broken without danger to the patient or to the surgeon. Another advantage of this invention is that firmness and/or distortions in shape produced by the scar capsules around a silicone bag implant for a human breast are improved.

For purposes of exemplification, a particular embodiment of the invention has been shown and described according to the best present understanding thereof. However, it will be apparent that changes and modifications in the arrangement and construction of the parts thereof may be resorted to without departing from the spirit and scope of the invention.

I claim:

1. An apparatus for breaking scar tissue within a human body including:
   force applying means to apply a continuous and increasing radially symmetrical force of substantially the same magnitude at each of a plurality of portions around an area having the scar tissue until the scar tissue breaks;
   said force applying means including:
      engaging means to engage the area having the scar tissue at each of a plurality of portions around the area, said engaging means including separate engaging means to engage each of the plurality of portions around the area;
      and moving means to simultaneously move all of said separate engaging means radially towards a central axis to continuously increase the force at each of the plurality of portions engaged by each of said separate engaging means until the scar tissue breaks.

2. The apparatus according to claim 1 in which:
   said engaging means includes:
      support means;
      a plurality of arms forming said separate engaging means so that each of said arms engages a portion around the area having the scar tissue;
      and pivotally mounted means to pivotally mount said arms on said support means;
   and said moving means moves each of said arms simultaneously in a radial direction towards the central axis to apply the force.

3. The apparatus according to claim 2 including main support means to support said moving means and said support means of said engaging means.

4. The apparatus according to claim 3 in which said main support means includes:
   first support means;
   and mounting means to mount said moving means and said support means of said engaging means on said first support means.

5. The apparatus according to claim 4 in which:
   said first support means includes horizontally disposed supports;
   and said mounting means of said main support means is mounted on said horizontally disposed supports for sliding movement therealong.

6. The apparatus according to claim 5 including tilting means to mount said force applying means on said mounting means of said main support means for tilting the body engaging plane of said arms.

7. The apparatus according to claim 6 in which:
   said pivotally mounted means of said engaging means pivotally mounts each of said arms adjacent its upper end to said support means of said engaging means;
   said support means of said engaging means is secured to said tilting means;
   and said moving means includes:
      a shaft extending through said tilting means and said support means of said engaging means, said shaft having threaded engagement with said support means of said engaging means;
      said shaft having means secured thereto for movement with said shaft along the longitudinal axis of said shaft when said shaft is moved longitudinally relative to said support means of said engaging means;
      and means pivotally connected to said secured means of said moving means and to each of said arms intermediate its ends to enable simultaneous pivoting of said arms towards the longitudinal axis of said shaft when said shaft moves longitudinally relative to said support means of said engaging means to cause each of said arms to apply an increasing radial force on the scar tissue against which said arms engage, the longitudinal axis of said shaft being the central axis.

8. The apparatus according to claim 7 in which said tilting means includes spherical means supported in said mounting means of said main support means for a ball and socket type of movement relative to said mounting means of said main support means.

9. The apparatus according to claim 8 in which:
   said mounting means of said main support means includes:
      a pair of plates;
      and each of said plates has an opening to receive a portion of said spherical means of said tilting means;
      and means to lock said plates of said mounting means of said main support means to each other to lock said spherical means of said tilting means in the position to which said shaft is tilted.

10. An apparatus for breaking scar tissue within a human body including:
force applying means to apply a continuous and increasing radially symmetrical force of substantially the same magnitude at each of a plurality of portions around an area having the scar tissue until the scar tissue breaks;
said force applying means including:
engaging means to engage the area having the scar tissue at each of a plurality of portions around the area;
and moving means to simultaneously move said engaging means radially towards a central axis;
said engaging means including:
support means;
a plurality of arms;
and pivotally mounted means to pivotally mount said arms on said support means;
said moving means moving each of said arms simultaneously in a radial direction towards the central axis;
main support means to support said moving means and said support means of said engaging means;
said main support means including:
first support means;
and mounting means to mount said moving means and said support means of said engaging means on said first support means;
said first support means of said main support means including horizontally disposed supports;
said mounting means of said main support means being mounted on said horizontally disposed supports for sliding movement therealong;
said first support means of said main support means including two pairs of support legs spaced from each other;
and means to slidably mount said horizontally disposed supports on said two pairs of support legs.

11. The apparatus according to claim 10 including means to lock said horizontally disposed supports to said two pairs of support legs of said first support means of said main support means.

12. The apparatus according to claim 11 including tilting means to mount said force applying means on said mounting means of said main support means for tilting the body engaging plane of said arms.

13. The apparatus according to claim 12 including means to move said horizontally disposed supports along said two pairs of legs of said first support means of said main support means when said locking means is ineffective.

14. The apparatus according to claim 13 in which:
said pivotally mounted means of said engaging means pivotally mounts each of said arms adjacent its upper end to said support means of said engaging means;
said support means of said engaging means is secured to said tilting means;
and said moving means includes:
a shaft extending through said tilting means and said support means of said engaging means, said shaft having threaded engagement with said support means of said engaging means;
said shaft having means secured thereto for movement with said shaft along the longitudinal axis of said shaft when said shaft is moved longitudinally relative to said support means of said engaging means;
and means pivotally connected to said secured means of said moving means and to each of said arms intermediate its ends to enable simultaneous pivoting of said arms towards the longitudinal axis of said shaft when said shaft moves longitudinally relative to said support means of said engaging means to cause each of said arms to apply an increasing radial force on the scar tissue against which said arms engage, the longitudinal axis of said shaft being the central axis.

15. The apparatus according to claim 14 in which said tilting means includes spherical means supported in said mounting means of said main support means for a ball and socket type of movement relative to said mounting means of said main support means.

16. The apparatus according to claim 15 in which:
said mounting means of said main support means includes:
a pair of plates;
and each of said plates has an opening to receive a portion of said spherical means of said tilting means;
and means to lock said plates of said mounting means of said main support means to each other to lock said spherical means of said tilting means in the position to which said shaft is tilted.

17. The apparatus according to claim 12 including means to lock said tilting means in the position to which the body engaging plane of said arms is tilted.

18. The apparatus according to claim 11 including means to move said horizontally disposed supports along said two pairs of legs of said first support means of said main support means when said locking means is ineffective.

19. The apparatus according to claim 10 including means to move said horizontally disposed supports along said two pairs of legs of said first support means of said main support means.

20. The apparatus according to claim 2 in which:
the number of said arms is even and at least four;
and each of said arms is disposed oppositely another of said arms so that opposite forces are applied by each pair of said arms that are oppositely disposed with the force being applied by each of said arms at the same time by said moving means simultaneously moving each of said arms in the radial direction towards the central axis.

21. The apparatus according to claim 3 including tilting means to mount said force applying means on said main support means for tilting the body engaging plane of said arms.

22. The apparatus according to claim 21 in which:
said pivotally mounted means of said engaging means pivotally mounts each of said arms adjacent its upper end to said support means of said engaging means;
said support means of said engaging means is secured to said tilting means;
and said moving means includes:
a shaft extending through said tilting means and said support means of said engaging means, said shaft having threaded engagement with said support means of said engaging means;
said shaft having means secured thereto for movement with said shaft along the longitudinal axis of said shaft when said shaft is moved longitudinally relative to said support means of said engaging means;

and means pivotally connected to said secured means of said moving means and to each of said arms intermediate its ends to enable simultaneous pivoting of said arms towards the longitudinal axis of said shaft when said shaft moves longitudinally relative to said support means of said engaging means to cause each of said arms to apply an increasing radial force on the scar tissue against which said arms engage, the longitudinal axis of said shaft being the central axis.

23. The apparatus according to claim 22 in which said tilting means includes spherical means supported by said main support means for a ball and socket type of movement relative to said main support means.

24. The apparatus according to claim 23 in which:
said main support means includes:
a pair of plates;
and each of said plates has an opening to receive a portion of said spherical means of said tilting means;
and means to lock said plates of said main support means to each other to lock said spherical means of said tilting means in the position to which said shaft is tilted.

25. The apparatus according to claim 21 including means to lock said tilting means in the position to which the body engaging plane of said arms is tilted.

26. The apparatus according to claim 4 including tilting means to mount said force applying means on said mounting means of said main support means for tilting the body engaging plane of said arms.

27. The apparatus according to claim 26 in which:
said pivotally mounted means of said engaging means pivotally mounts each of said arms adjacent its upper end to said support means of said engaging means;
said support means of said engaging means is secured to said tilting means;
and said moving means includes:
a shaft extending through said tilting means and said support means of said engaging means, said shaft having threaded engagement with said support means of said engaging means;
said shaft having means secured thereto for movement with said shaft along the longitudinal axis of said shaft when said shaft is moved longitudinally relative to said support means of said engaging means;
and means pivotally connected to said secured means of said moving means and to each of said arms intermediate its ends to enable simultaneous pivoting of said arms towards the longitudinal axis of said shaft when said shaft moves longitudinally relative to said support means of said engaging means to cause each of said arms to apply an increasing radial force on the scar tissue against which said arms engage, the longitudinal axis of said shaft being the central axis.

28. The apparatus according to claim 27 in which said tilting means includes spherical means supported in said mounting means of said main support means for a ball and socket type of movement relative to said mounting means of said main support means.

29. The apparatus according to claim 28 in which:
said mounting means of said main support means includes:
a pair of plates;
and each of said plates has an opening to receive a portion of said spherical means of said tilting means;
and means to lock said plates of said mounting means of said main support means to each other to lock said spherical means of said tilting means in the position to which said shaft is tilted.

30. The apparatus according to claim 26 including means to lock said tilting means in the position to which the body engaging plane of said arms is tilted.

31. The apparatus according to claim 6 including means to lock said tilting means in the position to which the body engaging plane of said arms is tilted.

32. The apparatus according to claim 12 in which:
said pivotally mounted means of said engaging means pivotally mounts each of said arms adjacent its upper end to said support means of said engaging means;
said support means of said engaging means is secured to said tilting means;
and said moving means includes:
a shaft extending through said tilting means and said support means of said engaging means, said shaft having threaded engagement with said support means of said engaging means;
said shaft having means secured thereto for movement with said shaft along the longitudinal axis of said shaft when said shaft is moved longitudinally relative to said support means of said engaging means;
and means pivotally connected to said secured means of said moving means and to each of said arms intermediate its ends to enable simultaneous pivoting of said arms towards the longitudinal axis of said shaft when said shaft moves longitudinally relative to said support means of said engaging means to cause each of said arms to apply an increasing radial force on the scar tissue against which said arms engage, the longitudinal axis of said shaft being the central axis.

33. The apparatus according to claim 32 in which said tilting means includes spherical means supported in said mounting means of said main support means for a ball and socket type of movement relative to said mounting means of said main support means.

34. The apparatus according to claim 33 in which:
said mounting means of said main support means includes:
a pair of plates;
and each of said plates has an opening to receive a portion of said spherical means of said tilting means;
and means to lock said plates of said mounting means of said main support means to each other to lock said spherical means of said tilting means in the position to which said shaft is tilted.

35. An apparatus for breaking scar tissue within a human body including:
force applying means to apply a continuous and increasing radially symmetrical force of substantially the same magnitude at each of a plurality of portions around an area having the scar tissue until the scar tissue breaks;
said force applying means including:
arm support means;

a plurality of arms for engaging the area having the scar tissue at each of a plurality of portions around the area;
pivotally mounted means to pivotally mount said arms on said support means;
and moving means to simultaneously move each of said arms in a radial direction towards a central axis to apply the continuous and increasing radially symmetrical force of substantially the same magnitude at each of the plurality of portions;
main support means to support said moving means and said arm support means;
and tilting means to mount said arm support means on said main support means for tilting the body engaging plane of said arms.

* * * * *

UNITED STATES PATENT AND TRADEMARK OFFICE
CERTIFICATE OF CORRECTION

PATENT NO. : 4,249,534

DATED : February 10, 1981

INVENTOR(S) : Louis M. Muldrow, Jr.

It is certified that error appears in the above—identified patent and that said Letters Patent is hereby corrected as shown below:

IN THE SPECIFICATION

Column 3, line 22, "And" should read --- and ---.

Column 4, line 26, "positions" should read --- portions ---.

Signed and Sealed this

Twenty-sixth Day of May 1981

[SEAL]

Attest:

RENE D. TEGTMEYER

*Attesting Officer*  *Acting Commissioner of Patents and Trademarks*